United States Patent [19]

Garber

[11] 4,107,170

[45] Aug. 15, 1978

[54] METHOD OF PREPARING dl 6-PHENYL-2,3,5,6-TETRAHYDROIMIDAZO-[2,1-b]THIAZOLE AND ACID ADDITION SALTS THEREOF

[75] Inventor: Murray Garber, Trenton, N.J.

[73] Assignee: American Cyanamid Company, Stamford, Conn.

[21] Appl. No.: 768,133

[22] Filed: Feb. 14, 1977

Related U.S. Application Data

[63] Continuation-in-part of Ser. No. 626,700, Oct. 29, 1975, abandoned, which is a continuation-in-part of Ser. No. 436,230, Jan. 24, 1974, abandoned, which is a continuation-in-part of Ser. No. 371,228, Jun. 18, 1973, abandoned.

[51] Int. Cl.$^2$ ............................................. C07D 513/04
[52] U.S. Cl. ............................................. 260/306.7 T
[58] Field of Search ................................. 260/306.7 T

[56] References Cited

U.S. PATENT DOCUMENTS

| 3,478,047 | 11/1969 | Doyle et al. | 260/306.7 T |
|---|---|---|---|
| 3,759,937 | 9/1973 | Baklien et al. | 260/306.7 T |
| 3,804,847 | 4/1974 | Mallion | 260/306.7 T |
| 3,804,847 | 4/1974 | Blakeney et al. | 260/306.7 T |
| 3,890,341 | 6/1975 | Gordon et al. | 260/306.7 T |

OTHER PUBLICATIONS

Morrison et al., Organic Chemistry, pp. 529–530, (1966).
Wagner et al., Synthetic Organic Chemistry, 1953, pp. 89–91.
Harrison, et al., Compendium of Organic Synthetic Reactions (1971), pp. 331–332.
Theilheimer, "Synthetic Methods," 1968, p. 273, set 590.

*Primary Examiner*—Donald G. Daus
*Assistant Examiner*—David E. Wheeler
*Attorney, Agent, or Firm*—Harry H. Kline

[57] ABSTRACT

An improved method of preparing acid addition salts of dl 6-phenyl-2,3,5,6-tetrahydroimidazo[2,1-b]thiazole (dl-tetramisole) by reacting dl-3-($\beta$-hydroxyphenethyl)-2-iminothiazolidine or an acid-addition salt thereof, with a mixture of concentrated hydrochloric acid and concentrated sulfuric acid to obtain dl 3-($\beta$-chlorophenethyl)-2-iminothiazolidine acid-addition salt, treating this compound with aqueous alkali to obtain dl 6-phenyl-2,3,5,6-tetrahydroimidazo[2,1-b]thiazole free base, and converting the latter compound to dl 6-phenyl-2,3,5,6-tetrahydroimidazo [2,1-b]thiazole acid-addition salts in a highly purified state. The products are useful as anthelmintics.

11 Claims, No Drawings

METHOD OF PREPARING dl 6-PHENYL-2,3,5,6-TETRAHYDROIMIDAZO-[2,1-b]THIAZOLE AND ACID ADDITION SALTS THEREOF

CROSS-REFERENCE TO RELATED APPLICATIONS

This application is a continuation-in-part of application Ser. No. 626,700, filed Oct. 29, 1975 now abandoned, which, in turn, was a continuation-in-part of application Ser. No. 436,230, filed Jan. 24, 1974, now abandoned, which, in turn, was a continuation-in-part of application Ser. No. 371,228, filed Jun. 18, 1973, now abandoned.

FIELD OF THE INVENTION

This invention relates to a process for the manufacture of dl 6-phenyl-2,3,5,6-tetrahydroimidazo[2,1-b]thiazole of the formula:

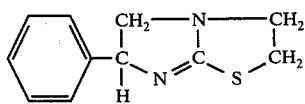

and therapeutically acceptable acid-addition salts thereof, such as the hydrochloride salt, by halogenating an acid-addition salt of the formula:

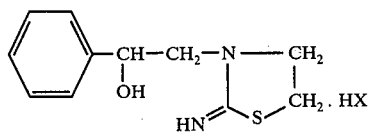

wherein HX is an acid such as hydrochloric, hydrobromic, or a sulfonic acid such as p-toluenesulfonic acid, or the free base thereof to produce the intermediate salt of the formula:

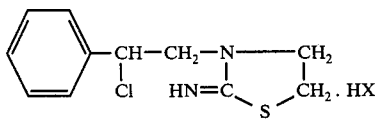

wherein HX is as described above.

More particularly, this invention relates to a method of preparing dl 6-phenyl-2,3,5,6-tetrahydroimidazo[2,1-b]thiazole hydrochloride, also known as dl-tetramisole hydrochloride, and improved methods of preparing intermediates therefor.

The dl 6-phenyl-2,3,5,6-tetrahydroimidazo[2,1-b]-thiazole hydrochloride prepared by the process of the present invention can be illustrated by the following formula:

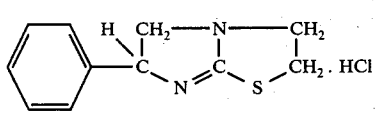

DESCRIPTION OF THE PRIOR ART

The preparation of dl-tetramisole hydrochloride by chlorination of dl-3-(β-hydroxyphenethyl)-2-iminothiazolidine hydrochloride and subsequent ring-closure is disclosed by Bullock U.S. Pat. No. 3,679,696. The process as disclosed therein is shown in Flowsheet 1.

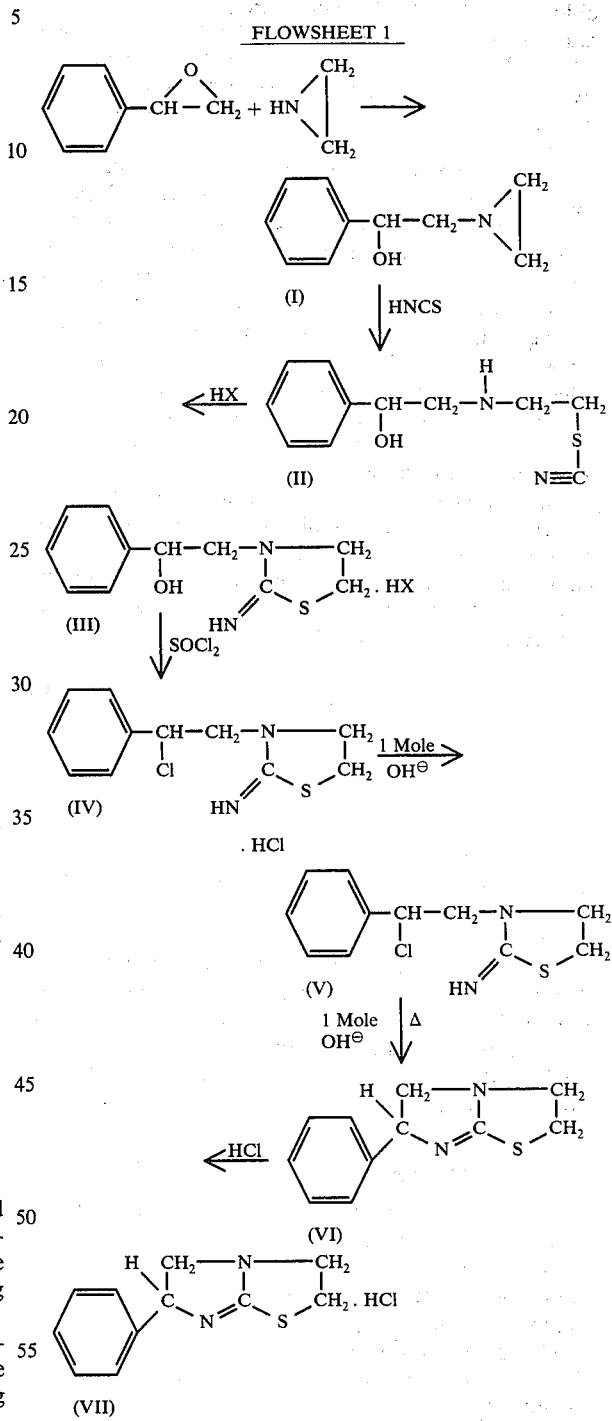

In the prior art process the intermediate dl-3-(β-hydroxyphenethyl)-2-iminothiazolidine is prepared by reacting α-phenyl-1-aziridineethanol, compound I, with either thiocyanic acid or thiourea and converted to the salt, compound III, by treatment with a strong acid. The preparation of compound I and the hydrochloride and p-toluenesulphonate salts of compound III are described by Baklien et al., Aust. J. Chem. 1968, 21, 1557-70.

The preparation of compound IV can be effected by heating compound III with thionyl chloride in an inert chlorinated hydrocarbon such as methylene chloride, chloroform or ethylene dichloride at 50° C. from several minutes to several hours and ring closing compound IV by treatment with an inorganic base. The overall yield from compound III to dl tetramisole hydrochloride, compound VII, is about 88 to 95% by this process.

The novel process of the present invention comprises the chlorination of dl-3-(β-hydroxyphenethyl)-2-iminothiazolidine, and acid addition salts thereof, in a mixture of at least two molar equivalent of concentrated aqueous hydrochloric acid of about 36% and at least one molar equivalent of sulfuric acid of about 94% to 98% to obtain the intermediate, dl-3-(β-chlorophenethyl)-2-iminothiazolidine. This is a distinct, terminable step which will occur without the formation of dl tetramisole as hereinbelow exemplified. The β-chloro analog is, in turn, cyclized by the known reaction with a suitable base to dl tetramisole.

An advantage of the novel chlorination process of the present invention is that it minimizes the transformation of compound (III), or the free base thereof, to trans-2-imino-3-styrylthiazolidine of formula (VIII), an undesirable impurity. The hydrochloride of compound (VIII) is referred to as the "styryl impurity".

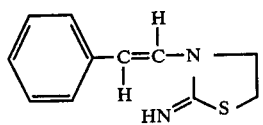

(VIII)

In contrast, chlorination of compound (III) effected by conventional halogenation agents, such as thionyl chloride, phosphorus trichloride, phosphorus pentachloride, and the like, have the disadvantage that relatively large (i.e., 0.3% to 5% or more) amounts of the "styryl impurity" are formed in the course of the reaction, and since this impurity is quite toxic its presence must be greatly reduced by further purification of the final product. This requires a complicated isolation procedure which greatly adds to the cost of the product.

SUMMARY OF THE INVENTION

In accordance with the process of the present invention, dl 6-phenyl-2,3,5,6-tetrahydroimidazo[2,1-b]thiazole hydrochloride is prepared in high yields containing acceptable (i.e., 0.2% or less) amounts of "styryl impurity" without further purification.

The process of the present invention is similar to that described in Flowsheet (1) up to and including the formation of the acid addition salt of dl-3-(β-hydroxyphenethyl)-2-iminothiazolidine, compound III.

Since compound III as prepared in the process described in Flowsheet (1) contains sodium chloride, the addition of sulfuric acid to the concentrated hydrochloric acid would assist the chlorination reaction by converting the residual sodium chloride to hydrogen chloride thus increasing the concentration of hydrogen chloride in the reaction mixture.

Although the addition of sodium chloride is not critical to this invention, i.e., compound III can be converted to dl tetramisole hydrochloride via compound IV without it, nevertheless slightly higher yields (2–5%) are obtained in the presence of sodium chloride.

The preparation of dl tetramisole hydrocloride from compound III by the process of this invention is outlined in Flowsheet (2). In the aforementioned Flowsheet (1), HX is defined as an acid capable of forming an addition salt with the free base of compound III. Illustrative of such acids are hydrochloric, hydrobromic and p-toluenesulfonic acid.

FLOWSHEET 2

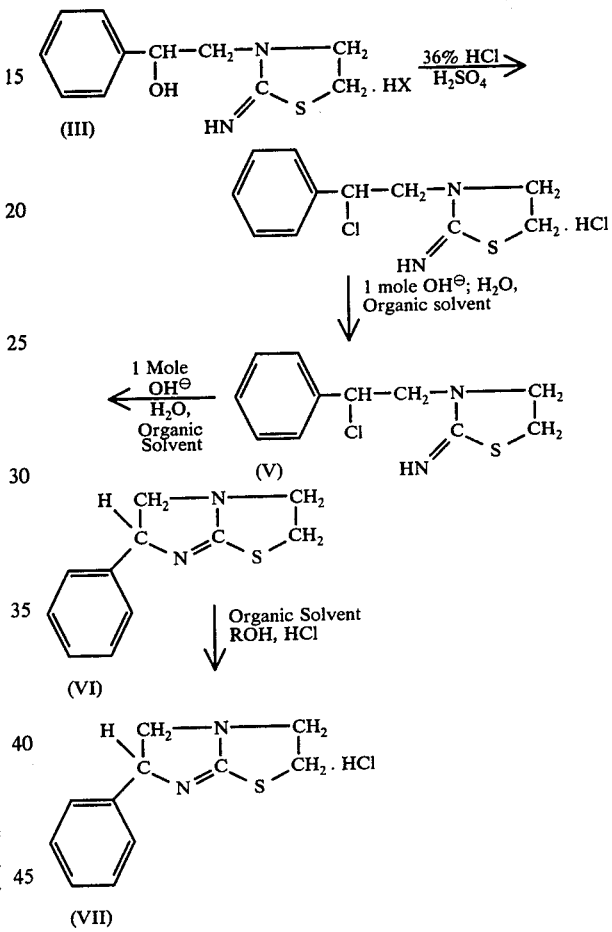

In the process of this invention, the chlorination of compound III may be carried out in a mixture prepared from at least two molar equivalent of about 36% concentrated hydrochloric acid (22° Be') and at least one molar equivalent of concentrated sulfuric acid (94–98%) at temperature ranging from 10° C to 70° C for a period of time ranging from 1 hour to 180 hours or more. Preferably, the chlorination reaction is carried out at a temperature ranging from 30° C to 50° C for a period of time ranging from 10 to 60 hours. This may be particularly accomplished by charging an autoclave with at least 2 molar equivalents of, but preferably 4 to 5 molar equivalents of concentrated aqueous hydrochloric acid of about 36% (22° Be'), cooling the acid from about 0° C to 5° C, adding 1 molar equivalent of compound III. Sodium chloride or potassium chloride may be added at this point if desired. The autoclave is closed, and at least 1 molar equivalent of, but preferably 2.5 to 5 molar equivalents of sulfuric acid of 94% to 98% is added at 0° C to 5° C. After completing the addition of the sulfuric acid, the contents are heated at 30° C to 50° C for a period of 10 to 60 hours.

On completion of the chlorination reaction, the reaction mixture is removed from the autoclave, diluted with water and admixed with a water-immiscible organic solvent or mixture of water-immiscible organic solvents, preferably an aromatic hydrocarbon such as toluene and a water-immiscible alcohol such as n-butanol.

The chlorination reaction mixture is then treated with an inorganic acid-binding agent such as aqueous caustic soda or potassium carbonate, at about 20° C to 30° C, to obtain a pH of about 5.0 to 7.5. The temperature of this reaction mixture is then raised to about 50° C to 60° C, and additional inorganic acid-binding agent is added thereto to maintain the pH of said mixture from about 7.5 to 9, and the reaction mixture is stirred at 50°-60° C. to effect ring closure to form compound VI. The mixture is then diluted with additional organic solvent, such as an aromatic hydrocarbon, i.e., toluene, and the aqueous layer is separated. The organic phase is clarified and the clarified solution is concentrated to recover dl 6-phenyl-2,3,5,6-tetrahydroimidazo[2,1-b]thiazole. If an acid addition salt, such as the hydrochloride, is required the clarified organic phase is acidified with an alcoholic solution of the anhydrous acid, such as isopropanolic hydrogen chloride, while maintaining the temperature between 0° and 40° C. The hydrogen chloride acidified reaction mixture is cooled to about 10° C., filtered and the filter cake is washed with isopropanol of ambient temperature. After drying at about 80° C. there is obtained a 98.9% yield of dl tetramisole hydrochloride, compound VII, based on the starting compound III. The quality of the product is satisfactory without further purification.

The process of this invention results in a much higher overall yield of dl tetramisole hydrochloride from the hydrochloride salt compound III, about 98% overall yield versus the 88% yield of the Bullock prior art or 79% of Doyle et al's process. In addition to the increase in yield, the process does not require the use of relatively expensive anhydrous hydrogen chloride and it does not require the complicated purification of the prior art because the dl tetramisole hydrochloride contains less than 0.2% trans-2-imino-3-styrylthiazolidine.

The process of this invention is particularly useful since the acid addition salts of dl tetramisole or l tetramisole are very useful as anthelmintics.

DETAILED DESCRIPTION

The following examples describe in detail the preparation of intermediates and their conversion to the desired final product of this invention.

EXAMPLE 1 dl-α-Phenyl-1-Aziridineethanol

To a solution of 43.0 g. (1.0 mole) of ethyleneimine and 60.0 g. (0.5 mole) of styrene oxide is added 3 drops of water and 0.2 g. of potassium hydroxide. The mixture is heated at reflux for 1½ hours. Distillation of the excess ethyleneimine from the crude product gives 55.6 g. (68%) of the crystalline product. Recrystallization gives pure dl-α-phenyl-1-aziridineethanol with melting point 74°-76° C.

EXAMPLE 2 dl-3-(β-Hydroxyphenethyl)-2-iminothiazolidine hydrochloride

One half of the crude product from the reaction of 1.0 mole of ethyleneimine with 0.50 mole of styrene oxide (Example 1) is reacted with thiocyanic acid without purification.

A warm mixture of 26.7 g. (0.275 mole) of potassium thiocyanate in 250 ml. of ethanol is treated with 53 g. of a methanolic solution of hydrogen chloride (0.25 mole). The precipitated potassium chloride is filtered, and washed with ethanol to provide the thiocyanic acid solution.

To the stirred solution of thiocyanic acid is added a solution of the crude dl-α-phenyl-1-aziridineethanol in 250 ml. of ethanol at a rate sufficient to keep the reaction temperature at 30°-35° C. After the aziridine addition is complete, 72 g. of a methanolic solution of hydrogen chloride (0.35 mole) is added and the solution stirred for 1.5 hours at room temperature. An additional 0.05 mole of hydrogen chloride in 10 g. of ethanol is added, and the reaction heated at 35°-40° C. for 0.5 hour. It is then allowed to proceed at room temperature for 2.5 days. The mixture is concentrated under reduced pressure to about 100 ml., filtered, washed with ethanol and dried to give 27.1 g. of white crystals, melting point 198°-200° C. The yield is 42% (based on styrene oxide) or 71% (based on dl-α-phenyl-1-aziridineethanol).

EXAMPLE 3

A laboratory pressure bottle is charged with 75 ml. of concentrated hydrochloric acid (22° Be'), cooled to 0°-5° C. and 52 g. of 95% sulfuric acid (0.5 mole) is added thereto. An amount of 49.1 g. of real dl-3-(β-hydroxyphenethyl)-2-iminothiazolidine hydrochloride, compound III, (0.19 mole) plus 23.4 g. of sodium chloride (0.4 mole) is added at 0°-5° C. the pressure bottle is closed and the contents heated at 45°-47° C. for 22 hours. The reaction mixture is then cooled and added to a mixture of 188 ml. of water, 27 ml. of n-butanol and 38 ml. of toluene. The mixture is agitated at 15°-20° C. and 50% sodium hydroxide solution is added thereto dropwise to adjust the pH to 6. The mixture is then heated to 50°-55° C., 39.4 g. (0.285 mole) of anhydrous potassium carbonate is added quickly and the mixture is stirred at 50°-55° C. for 2 hours. At the end of this time, an additional 50 ml. of toluene is added thereto, the water layer is separated and the organic layer is clarified. The clarified organic layer is treated with a solution of isopropanolic hydrogen chloride below 40° C. to the point where Congo Red test paper changes from red to blue. The solution is then cooled to 10° C., filtered and the filter cake is washed with 100 ml. of ambient temperature isopropanol. The product is then dried at 80° C. to obtain 45.2 g. of dl tetramisole hydrochloride, compound VII, which represents a 98.9% overall yield based on the starting compound III. The product contained 0.15% by weight of styryl impurity VIII.

EXAMPLE 4

The procedure of Example 3 is followed except that 1.0 mole of sulfuric acid is added per mole of sodium chloride present in the starting compound III. The overall yield based on real starting compound III is 93.7% of theory. The product contains 0.15% by weight of styryl impurity.

EXAMPLE 5

This example illustrates that a lower yield is obtained in the absence of sulfuric acid even when the chlorination reaction is prolonged.

A laboratory pressure bottle is charged with 75.0 g. of material which contains 15.5 g. of sodium chloride and 49.2 g. of real dl 3-(β-hydroxyphenethyl)-2-iminothiazolidine hydrochloride, and 116 ml. of 36% hydrochloric acid (22° Be') and the mixture is heated at 45°-47° C. for 70 hours. At the end of this time, the reaction mixture is cooled and worked up in the same manner as in Example 3. The yield of dl 6-phenyl-2,3,5,6-tetrahydroimidazo[2,1-b]thiazole hydrochloride based on starting material charged is 80% of theory.

EXAMPLE 6

To a 500 ml. flask is added 91.8 g. (78 ml; 0.93 mole) of 37% aqueous hydrochloric acid, and 79.0 g. (0.2 mole) of dl-3-(β-hydroxyphenethyl)-2-iminothiazolidine III, as the p-toluene-sulfonate salt. The flask vents are sealed, and 55.8 g. of 97% sulfuric acid (30.5 ml; 0.57 mole) is added to the reaction mixture over a period of one hour while stirring and maintaining a temperature of 30°-32° C. with external cooling. After the addition of the sulfuric acid is completed, the reaction mixture is heated and held at 40°-46° C. for 20 hours. Samples of the crude reaction mixture are taken after 2, 4, and 20 hours, respectively. The samples, after diluting with water, adjusting the pH to 3 with ammonium hydroxide and then diluting with methanol, are spotted on thin layer plates (Silica Gel F-254) and developed in a 50:50:1.5 acetone:toluene:ammonium hydroxide solvent system. The developed plates clearly show that the major product in all three samples is dl-3-(β-chlorophenethyl)-2-iminothiazolidine-p-toluenesulfonate, IV. Essentially no dl tetramisole, VI, and very little unreacted dl-3-(β-hydroxyphenethyl)-2-iminothiazolidine, III, is present. A small portion of the reaction mixture is diluted with water, and the product is filtered. The isolated material on recrystallization from ethanol is identical to an authentic sample of dl-(β-chlorophenethyl)-2-iminothiazolidine-p-toluenesulfonate, IV, by infrared analysis and melting point (200°-201° C.).

The main portion of the reaction mixture containing the chlorinated compound, IV, (0.195 moles as III), is added to a 2-liter flask containing 750 ml. of water and 250 ml. of toluene. While stirring, 50% sodium hydroxide is added at 55°-60° C. until the pH is stabilized at 9-9.5; a total of 118 ml. of 50% sodium hydroxide is required. The toluene phase is separated from the aqueous phase, clarified by filtration, and dl tetramisole hydrochloride is precipitated by the addition thereto of isopropanolic hydrogen chloride until a blue color is obtained with Congo Red indicator paper. On cooling to 10° C., the dl tetramisole hydrochloride is separated by filtration and washed with isopropanol. After air drying, a total of 42.7 g. (91% yield) of dl tetramisole hydrochloride is obtained which melts at 258°-262° C. The product contains less than 0.2% by weight of the styryl impurity, VIII.

EXAMPLE 7

A laboratory pressure bottle is charged with 92 ml. of 37% hydrochloric acid, cooled to 0°-5° C., and a mixture consisting of 79.0 g. (0.2 mole) of dl-3-(β-hydroxyphenethyl)-2-iminothiazolidine-p-toluene sulfonate and 40.4 g. (0.69 mole) of sodium chloride is added. The mixture is cooled to 0°-5° C., and 89.2 g. of 97% sulfuric acid (0.875 mole) is added. The pressure bottle is closed, and the contents heated at 50° C. for 20 hours. The reaction mixture is cooled and added to a mixture of 200 ml. water and 250 ml. of toluene. The mixture is agitated at 20°-30° C. and 50% sodium hydroxide solution is added thereto dropwise to adjust the pH to 6. The mixture is heated to 50°-55° C., 40.0 g. of anhydrous potassium carbonate is added quickly, and the mixture is stirred at 50°-55° C. for 2 hours. At the end of this time, an additional 100 ml. of water is added, the lower aqueous layer separated, and the organic layer clarified. The clarified organic layer is treated with a solution of isopropanolic hydrogen chloride below 40° C. to the point where Congo Red test paper changes from red to blue. The reaction mixture is then cooled to 10° C., the precipitate is separated by filtration, and filter cake washed with 100 ml. of ambient temperature isopropanol. The product is air dried to constant weight to obtain 44.4 g. (92.5% yield) of dl tetramisole hydrochloride, compound VII. The product contains less than 0.1% of the styryl impurity, VIII.

EXAMPLE 10

Preparation of dl-3-(β-chlorophenethyl)-2-iminothiazolidine p-toluenesulfonate A sample of dl-3-(β-hydroxyphenethyl)-2-iminothiazolidine-p-toluenesulfonate (7.9 g., 0.019 mole), concentrated hydrochloric acid (37% aqueous; 10 ml., 0.09 mole) and sodium chloride (4.0 g.) are mixed in a pressure vessel and cooled to 0° C. to 5° C. Concentrated sulfuric acid (96%; 5 ml., 0.057 mole) is added to the mixture in a closed system over 1 hour at 0° C. to 5° C. The reaction mixture is heated in 15 minutes to 45° C. to 50° C. and held at 48° C. for 5 hours. It is then cooled down and stirred overnight in a closed system. The pressure is then released and the reaction mixture poured on an ice/water mixture. The precipitate formed is collected by filtration, washed and dried to afford 7.9 g. white solid (95.8% yield). Infrared analysis shows the sample to be identical to an authentic sample of dl-3-(β-chlorophenethyl)-2-iminothiazolidine p-toluenesulfonate. A sample recrystallized from methanol has a m.p. of 198° to 200° C.

No dl tetramisole is found in the reaction mixture by thin layer chromatography.

EXAMPLE 11

Preparation of dl Tetramisole Hydrochloride from dl-3-(β-chlorophenethyl)-2-iminothiazolidine p-toluenesulfonate A mixture of dl-3-(β-chlorophenethyl)-2-iminothiazolidine-p-toluenesulfonate (2.0 g., 0.0048 mole), water (25 ml.) and toluene (25 ml.) is stirred, cooled to 0° C. and sodium hydroxide (50% aqueous) added slowly at 0° C. until the pH of the reaction mixture stabilizes at 9.

The toluene layer is separated, clarified and a mixture of 2-propanol/hydrochloric acid added to the point where Congo Red test paper changes from red to blue. The mixture is heated to reflux, cooled and filtered. The crystalline solid obtained is air dried to afford dl tetramisole hydrochloride (1.1 g., 96.5% yield). Infrared analysis shows the sample to be identical to an authentic sample of dl tetramisole hydrochloride.

I claim:

1. An improved process for the preparation of dl-6-phenyl-2,3,5,6-tetrahydroimidazo[2,1-b]thiazole and acid-addition salts thereof represented by formula (I):

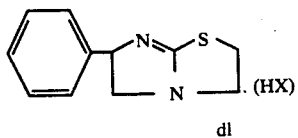

wherein the acid HX is selected from the group consisting of hydrochloric acid, hydrobromic acid and p-toluenesulfonic acid; comprising the following reaction sequence: (a) replacing the hydroxy group of dl-3-(β-hydroxyphenethyl)-2-iminothiazolidine and acid-addition salts thereof represented by formula (II):

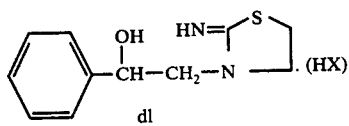

wherein HX is as hereinabove defined; with a chloro group by dissolving said formula (II) compound or an acid-addition salt thereof in a chlorination mixture prepared from at least 2 molar equivalent of concentrated aqueous hydrochloric acid of about 36% and at least 1 molar equivalent of sulfuric acid of about 94% to 98%, maintaining said solutions at a temperature range from 10° C. to 70° C. until the chlorination is essentially completed to obtain a solution of dl-3-(β-chlorophenethyl)-2-iminothiazolidine represented by formula (III):

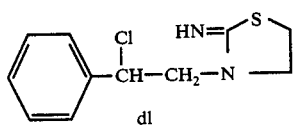

in said acidic chlorination mixture; (b) diluting said acidic chlorination mixture with water, adding a water-immiscible organic solvent and ring-closing said formula (III) dl-3-(β-chlorophenethyl)-2-iminothiazoline to dl-6-phenyl-2,3,5,6-tetrahydroimidazo[2,1-b]thiazole by intramolecularly removing the elements of hydrochloric acid therefrom with a inorganic alkali metal base added to the above acidic solutions of said formula (III) compound in sufficient quantity to increase to, and maintain the pH of said mixture from about 7.5 to 9 at a temperature range from about 20° C. to 55° C., and recovering said formula (I) dl-6-phenyl-2,3,5,6-tetrahydroimidazo[2,1-b]thiazole base from the water-immiscible organic solvent phase, or converting said formula (I) compound to its HX salt, by adding a mixture of the appropriate HX acid as hereinabove defined and a lower $C_1$-$C_4$ alcohol to said organic solvent phase.

2. The process according to claim 1, wherein (a) formula (II) dl-3-(β-hydroxyphenethyl)-2-iminothiazoline or an acid-addition salt thereof is chlorinated in a mixture prepared from 4 to 5 molar equivalents of concentrated aqueous hydrochloric acid of about 36% and 2.5 and 5 molar equivalents of sulfuric acid of 94% to 98% at a temperature range from 30° C. to 50° C.; and (b) said formula (III) dl-3-(β-chlorophenethyl)-2-iminothiazolidine is ring-closed to formula (I) dl-6-phenyl-2,3,5,6-tetrahydroimidazo[2,1-b]thiazole with sodium hydroxide or potassium carbonate or mixtures thereof, at a temperature range from 50° C. to 60° C.

3. The process according to claim 1, wherein the acid-addition salt of dl-3-(β-hydroxyphenethyl)-2-iminothiazolidine is the hydrochloride.

4. The process according to claim 1, wherein the acid-addition salt of dl-3-(β-hydroxyphenethyl)-2-iminothiazolidine is the p-toluenesulfonate.

5. A method according to claim 1, wherein the temperature of step (a) ranges from 30° to 50° C. and is maintained for a period of 10 hours to 60 hours.

6. A method according to claim 1, wherein the water-immiscible organic solvent of step (b) is a mixture of an aromatic hydrocarbon and a water-immiscible alcohol.

7. A method according to claim 1, wherein the inorganic acid-binding agents of step (b) are alkali metal hydroxide or carbonates.

8. A method according to claim 1, wherein the thus formed dl-6-phenyl-2,3,5,6-tetrahydroimidazo[2,1-b]thiazole is treated with hydrochloric acid in the presence of an organic solvent and at a temperature between 0° and 40° C. whereby dl-6-phenyl-2,3,5,6-tetrahydroimidazo[2,1-b]thiazole hydrochloride is formed.

9. A method for preparing dl-6-phenyl-2,3,5,6-tetrahydroimidazo[2,1-b]thiazole hydrochloride comprising the steps of (1) admixing dl-3-(β-hydroxyphenethyl)-2-iminothiazolidine, or an acid-addition salt thereof, with concentrated hydrochloric acid (22° Be'), and concentrated sulfuric acid (94% to 98%), (2) maintaining said reaction mixture at a temperature between 30° C. and 50° C. for a period of 10 to 60 hours, (3) adding to the reaction mixture, a mixture of water, toluene and n-butanol, (4) adjusting the pH of the reaction mixture to about 5 to 7 by the addition of aqueous sodium hydroxide at room temperature, (5) heating the neutralized reaction mixture at a temperature from 50° to 55° C., with about a stoichiometric amount of potassium carbonate, (6) separating the organic phase, (7) acidifying the organic phase with an alcoholic solution of hydrogen chloride, and (8) separating the precipitated dl-6-phenyl-2,3,5,6-tetrahydroimidazo[2,1-b]thiazole hydrochloride.

10. A method according to claim 9, wherein the acid-addition salt of dl-3-(β-hydroxyphenethyl)-2-iminothiazolidine is the hydrochloride.

11. A method according to claim 9, wherein the acid-addition salt of dl-3-(β-hydroxyphenethyl)-2-iminothiazolidine is the p-toluenesulfonate.

* * * * *